United States Patent [19]
Rossi

[11] Patent Number: 5,985,923
[45] Date of Patent: Nov. 16, 1999

[54] COMPOSITION FOR TREATING POULTRY LITTER

[75] Inventor: Jean Rossi, Bellevue, Switzerland

[73] Assignee: Crina S.A., Gland, Switzerland

[21] Appl. No.: 09/051,662

[22] PCT Filed: Oct. 10, 1996

[86] PCT No.: PCT/IB96/01065

§ 371 Date: May 13, 1998

§ 102(e) Date: May 13, 1998

[87] PCT Pub. No.: WO97/14298

PCT Pub. Date: Apr. 24, 1997

[30] Foreign Application Priority Data

Oct. 19, 1995 [CH] Switzerland .............................. 2967/95

[51] Int. Cl.$^6$ ......................... A61K 31/22; A61K 31/225; A61K 31/19

[52] U.S. Cl. .......................... 514/546; 514/547; 514/548; 514/549; 514/557

[58] Field of Search ..................................... 424/438, 442; 514/546, 547, 548, 549, 557

[56] References Cited

U.S. PATENT DOCUMENTS

| | | | |
|---|---|---|---|
| 5,208,257 | 5/1993 | Kabara | 514/552 |
| 5,280,042 | 1/1994 | Lopes | 514/557 |
| 5,558,889 | 9/1996 | Rossi | 426/89 |
| 5,565,211 | 10/1996 | Rossi | 424/438 |

FOREIGN PATENT DOCUMENTS

| | | |
|---|---|---|
| 0 338 398 | 10/1989 | European Pat. Off. . |
| 2 108 389 | 5/1983 | United Kingdom . |
| 9613175 | 5/1996 | WIPO . |

*Primary Examiner*—Kevin E. Weddington
*Attorney, Agent, or Firm*—Young & Thompson

[57] ABSTRACT

The composition for the treatment of poultry litters comprises at least an edible surfactant emulsifying agent, for example an ethoxylate obtained from castor oil. It may also be combined with a mixture of cresols, guaiacol and resorcinol. This composition can be sprayed in liquid form on the litter so as to reduce the effects of coccidiose.

9 Claims, No Drawings

COMPOSITION FOR TREATING POULTRY LITTER

FIELD OF THE INVENTION

The present invention relates to a composition for the treatment of poultry litter, as well as to a process for the use of this composition, so as to reduce the negative effects of coccidiosis in poultry.

BACKGROUND OF THE INVENTION

Coccidiosis is an illness particularly of poultry due to the infection arising from one or several species of coccidiae or protozoa of large size of the sporozoa type. These protozoa, frequent in poultry raising, are ingested by animals in the form of sporulated oocyst. They thus undergo in the digestive tract of animals a cycle of development and multiplication such that, starting from several sporulated oocysts, there are excreted in fecal material millions of non-sporulated oocysts. The non-sporulated oocysts, which are not infectious, are transformed during their stay in fecal material after excretion, and hence in the litter, into sporulated infectious oocysts. But only a portion of the non-sporulated oocysts are transformed into sporulated oocysts; however, the degree of sporulation depends on the composition of the fecal materials: moisture content, oxygen content, pH, etc. If sporulation is intense, the reinfected animals will perish or will experience very reduced growth and production. If sporulation is moderate, the animals will suffer only a slight infection and thus are immunized.

The object of the present invention therefore is to provide a composition adapted to be incorporated in poultry litter, whose action is based on the reduction of sporulation of the oocysts in said litter and permits practically preventing the pathogenic reinfection of the poultry.

There are already known from GB-A-2 108 389 disinfectant compounds for the treatment of litter which contain as a biocidal agent an alkyl benzene sulfonic acid dissolved in an oily hydrophobic base. Such compositions are adapted to act only on the litter itself, and the disinfectant agent that they contain can be harmful to the animals that ingest it.

SUMMARY OF THE INVENTION

However, the present inventor has shown that the incorporation in litter of at least one suitable edible surfactant emulsifier permits obtaining in an altogether unforeseeable manner the results sought by the present invention to reduce significantly the negative effects of coccidiosis in poultry, more particularly by decreasing the sporulation of the oocysts which gives rise to serious lesions due to infected litter.

DETAILED DESCRIPTION OF THE INVENTION

Thus, the composition for the treatment of poultry litter according to the present invention and which achieves the above object, comprises at least one edible surface active emulsifying agent.

The emulsifying agents can be present in the form of water-soluble powder or in liquid form, containing 10 to 100% of said agents; in both cases, the powder or the liquid will be placed in aqueous solution before use. As a support for the powder, can be used for example dextrose, whilst the liquid form is for example in water or propylene-glycol.

The emulsifier or emulgator can be selected preferably from among those which are tolerated by the biological systems and which are mostly hydrophilic in nature, for example esters, polyglycerol esters, and sorbitol esters of fatty acids, such as fatty acid ethoxylates in the form of mono-, di- and triesters of oleic acid, ethoxylates of mono-, di- and triglycerides, ethoxylates of mono- or diesters of sorbitol and fatty acids such as oleic acid or ricinoleic acid, obtained from fatty acids of tallow, soy oil, rape seed oil, castor oil or linseed oil, or coconut oil; and ethoxylated alcohols; etc., the ethoxylates obtained from castor oil being more particularly preferred.

The treatment of litter by the composition according to the invention can take place by a simple spraying on the litter of the liquid composition, in the amount of 20 to 100 ml per $m^2$ of litter, using one or the other of the mentioned forms after 4 to 5 fold dilution. More particularly, the edible surfactant agents are incorporated in the litter in an amount of 0.2 to 5.0 g per $m^2$, preferably 0.5 to 2 $g/m^2$.

As a modification, the edible surfactant emulsifier can be combined with a mixture of cresols, guaiacol, and resorcinol, and if desired with one or several of the following components: tannin, thymol, eugenol and anethole.

By way of example, such a composition in the form of a liquid can comprise 2.5 to 20 mg of cresols, 2.5 to 20 mg of guaiacol, 2.5 to 20 mg of resorcinol, and from 200 to 2000 mg of surfactant emulsifier, as well as 0 to 20 mg of tannin, thymol, eugenol and/or anethole.

The present invention will now be illustrated in greater detail with reference to the following example.

EXAMPLE (1) Preparation of the compositions

There was prepared by simple mixing of the respective components, the two liquid compositions A and B as follows:

A: 2 g of ethoxylated castor oil is dissolved in water (7 ml) and propyleneglycol (1 ml), then the solution is diluted for spraying over one square meter of litter.

B: 2 g of ethoxylated castor oil and 1 ml of propyleneglycol, in which have been dissolved 5 mg of guaiacol, 5 mg of resorcinol and 5 mg of m-cresol, are dissolved in 7 ml of water, then the solution is diluted for spraying over one square meter of liter.

(2) Comparative laboratory tests

A convention litter for poultry was infected with non-sporulated E. Tenella with a population of 5,000,000 oocysts/$m^2$, and was separated into three portions. The two first portions were each treated by one of the compositions according to composition A, respectively B, whilst the third was not treated (control).

After 24 hours, the oocysts were recovered, water was added and they were maintained at 28° C. for 48 hours for sporulation.

The three solutions obtained were then inoculated into three groups of chicks. After 7 days, the animals were sacrificed, and the lesions were observed and quantified according to the criteria of J. Johnson and W. M. Reid (Experimental Parasitology, 28(1), 30–36):

| | |
|---|---|
| 0 | no macroscopic lesion |
| 1 | very slight lesions |
| 2 | several lesions |
| 3 | numerous lesions |
| 4 | very numerous lesions |

The observations carried out gave the following results, in percentages, relative to the three inoculated solutions obtained from litters treated with A, B and the untreated litter.

| Seriousness of Lesions | Untreated Litter (control) | Litter Treated With | |
|---|---|---|---|
| | | Comp. A | Comp. B |
| 0 | 0 | 0 | 0 |
| 1 | 0 | 0 | 25% |
| 2 | 0 | 25% | 25% |
| 3 | 50% | 50% | 50% |
| 4 | 50% | 25% | 0 |

It will clearly be seen from the obtained results that the sporulation of the oocysts has been substantially reduced by preliminary treatment of the litters by means of the composition according to the invention designated A and B, and that the addition of phenols (cresol, guaiacol and resorcinol) has improved the effect of the surfactant agent, because the seriousness of the lesions has been reduced.

The results therefore confirm clearly that the treatment oultry litters by the compositions according to the invention permits reducing significantly the infective power of the oocysts in said litter, and thereby greatly to contribute to decreasing the negative effects of coccidiosis in poultry.

Finally, it is also possible to combine the treatment of the litter by means of the composition according to the invention, with an anti-coccidiosis treatment in foodstuffs for poultry, with the conventional coccidiostats.

I claim:

1. A composition for the treatment of poultry litter so as to reduce the effects of coccidiosis, comprising at least one edible surfactant emulsifying agent.

2. A composition according to claim 1 containing from 10 to 100% of surfactant agents, in the form of a water-soluble powder or in the form of concentrated liquid.

3. A composition according to claim 1, in which the emulsifying agent is selected from the group consisting of esters, polyglycerol esters and sorbitol esters of fatty acids, ethoxylates of fatty acids in the form of mono-, di- and triesters of oleic acid, ethoxylates of mono-, di- and triglycerides, ethoxylates of mono- or diesters of sorbitol and fatty acids of oleic acid or castor oil, obtained from tallow fatty acids, soy oil, rape seed oil, castor oil or linseed oil, or from coconut oil, and ethoxylated alcohols.

4. A composition according to one of claims 1, which comprises a mixture of cresols, guaiacol and resorcinol, in combination with said surface active emulsifying agent.

5. A composition according to claim 4 comprising also one or several of the following compounds: tannin, thymol, eugenol and anethole.

6. A composition according to claim 5, comprising 2.5 to 20 mg of cresols, 2.5 to 20 mg of guaiacol, 2.5 to 20 mg of resorcinol, and from 200 to 2000 mg of edible surfactant emulsifier, as well as 0 to 20 mg of tannin, thymol, eugenol and/or anethole.

7. A process for the treatment of poultry litter so as to reduce the effects of coccidiosis, which comprises: spraying over the litter from 20 to 100 ml/m$_2$ of litter, the composition according to claim 1, in liquid form.

8. A process for the treatment of poultry litter, which comprises incorporating in the litter at least one edible surfactant emulsifying agent in an amount of 0.2 to 5.0 g per m$^2$.

9. A process according to claim 8, wherein the edible surfactant emulsifying agent is incorporated in the litter in the amount of 0.5 to 2 g/m$^2$.

* * * * *